(12) United States Patent
Sato et al.

(10) Patent No.: US 7,501,512 B2
(45) Date of Patent: Mar. 10, 2009

(54) CHEMICAL COMPOUNDS

(75) Inventors: Hideyuki Sato, Tsukuba (JP); Mio Takada, Tsukuba (JP); Yoshiaki Washio, Tsukuba (JP)

(73) Assignee: SmithKline Beecham Corporation, Philadelphia, PA (US)

( * ) Notice: Subject to any disclaimer, the term of this patent is extended or adjusted under 35 U.S.C. 154(b) by 280 days.

(21) Appl. No.: 10/564,123

(22) PCT Filed: Jul. 7, 2004

(86) PCT No.: PCT/US2004/021701

§ 371 (c)(1),
(2), (4) Date: Jan. 6, 2006

(87) PCT Pub. No.: WO2005/007092

PCT Pub. Date: Jan. 27, 2005

(65) Prior Publication Data

US 2006/0178384 A1    Aug. 10, 2006

Related U.S. Application Data

(60) Provisional application No. 60/485,365, filed on Jul. 8, 2003.

(51) Int. Cl.
C07D 239/00 (2006.01)
C07D 239/70 (2006.01)
C07D 471/00 (2006.01)
C07D 487/00 (2006.01)

(52) U.S. Cl. .................................................. 544/252

(58) Field of Classification Search ................ 544/252; 514/267

See application file for complete search history.

(56) References Cited

U.S. PATENT DOCUMENTS

| 3,976,055 | A |   | 8/1976  | Monter et al. |
| 4,244,779 | A |   | 1/1981  | Neiminen et al. |
| 4,311,670 | A |   | 1/1982  | Neiminen et al. |
| 4,482,556 | A |   | 11/1984 | Lal et al. ............ 424/251 |
| 4,581,172 | A |   | 4/1986  | Kaiser et al. |
| 4,598,148 | A | * | 7/1986  | Lal et al. ............ 544/252 |
| 5,141,936 | A |   | 8/1992  | Rupp et al. |

FOREIGN PATENT DOCUMENTS

| DE | 199 35 209.7 | 7/1999 |
| EP | 370379       | 9/1992 |
| IN | 149457       | 12/1979 |
| WO | WO95/09636   | 4/1995 |
| WO | WO98/45293   | 4/1998 |

OTHER PUBLICATIONS

Xiao, et al., Differential roles of checkpoint kinase 1, checkpoint kinase 2, and mitogen-activated protein kinase-activated protein kinase 2 in mediating DNA damage-induced cell cycle arrest: implications for cancer therapy. Molecular cancer therapeutics, (Aug. 2006) vol. 5, No. 8, pp. 1935-1943.*

West, Anthony R., Solid State Chemistry and Its Applications, Wiley, New York, 1988, 358.*

* cited by examiner

Primary Examiner—James O Wilson
Assistant Examiner—Erich A Leeser
(74) Attorney, Agent, or Firm—John L. Lemanowicz; William T. Han

(57) ABSTRACT

This invention relates to newly identified inhibitors of kinases for treating various disorders.

26 Claims, No Drawings

US 7,501,512 B2

CHEMICAL COMPOUNDS

This Application is a §371 of International Application No. PCT/US04/021701, filed 07 Jul. 2004, which claims priority of U.S. Provisional Application No. 60/485,365, filed 08 Jul. 2003.

FIELD OF THE INVENTION

This invention relates to newly identified inhibitors of kinases for treating various disorders.

BACKGROUND OF THE INVENTION

A number of polypeptide growth factors and hormones mediate their cellular effects through a signal transduction pathway. Transduction of signals from the cell surface receptors for these ligands to intracellular effectors frequently involves phosphorylation or dephosphorylation of specific protein substrates by regulatory protein serine/threonine kinases (PSTK) and phosphatases. Serine/threonine phosphorylation is a major mediator of signal transduction in multicellular organisms. Receptor-bound, membrane-bound and intracellular PSTKs regulate cell proliferation, cell differentiation and signalling processes in many cell types.

Aberrant protein serine/threonine kinase activity has been implicated or is suspected in a number of pathologies such as rheumatoid arthritis, psoriasis, septic shock, bone loss, many cancers and other proliferative diseases. Accordingly, serine/threonine kinases and the signal transduction pathways which they are part of are potential targets for drug design.

A subset of PSTKs are involved in regulation of cell cycling. These are the cyclin-dependent kinases or CDKs (Peter and Herskowitz, Cell 1994: 79, 181-184). CDKs are activated by binding to regulatory proteins called cyclins and control passage of the cell through specific cell cycle checkpoints. For example, CDK2 complexed with cyclin E allows cells to progress through the G1 to S phase transition. The complexes of CDKs and cyclins are subject to inhibition by low molecular weight proteins such as p16 (Serrano et al, Nature 1993: 366, 704), which binds to and inhibits CDK4. Deletions or mutations in p16 have been implicated in a variety of tumors (Kamb et al, Science 1994: 264, 436-440). Therefore, the proliferative state of cells and diseases associated with this state are dependent on the activity of CDKs and their associated regulatory molecules. In diseases such as cancer where inhibition of proliferation is desired, compounds that inhibit CDKs may be useful therapeutic agents. Conversely, activators of CDKs may be useful where enhancement of proliferation is needed, such as in the treatment of immunodeficiency.

YAK1, a PSTK with sequence homology to CDKs, was originally identified in yeast as a mediator of cell cycle arrest caused by inactivation of the cAMP-dependent protein kinase PKA (Garrett et al, Mol Cell Biol. 1991: 11, 4045-4052). YAK1 kinase activity is low in cycling yeast but increases dramatically when the cells are arrested prior to the S-G2 transition. Increased expression of YAK1 causes growth arrest in yeast cells deficient in PKA. Therefore, YAK1 can act as a cell cycle suppressor in yeast.

Our U.S. Pat. No. 6,323,318 describes two novel human homologs of yeast YAK1 termed hYAK3-2, one protein longer than the other by 20 amino acids. hYAK3-2 proteins (otherwise reported as REDK-L and REDK-S in *Blood*, 1 May 2000, Vol 95, No. 9, pp 2838) are primarily localized in the nucleus. hYAK-2 proteins (hereinafter simply referred as hYAK3 or hYAK3 proteins) are present in hematopoietic tissues, such as bone marrow and fetal liver, but the RNA is expressed at significant levels only in erythroid or erthropoietin (EPO)-responsive cells. Two forms of REDK cDNAs appear to be alternative splice products. Antisense REDK oligonucleotides promote erythroid colony formation by human bone marrow cells, without affecting colony-forming unit (CFU)-GM, CFU-G, or CFU-GEMM numbers. Maximal numbers of CFU-E and burst-forming unit-erythroid were increased, and CFU-E displayed increased sensitivity to suboptimal EPO concentrations. The data indicate that REDK acts as a brake to retard erythropoiesis. Thus inhibitors of hYAK3 proteins are expected to stimulate proliferation of cells in which it is expressed. More particularly, inhibitors of hYAK3 proteins are useful in treating or preventing diseases of the erythroid and hematopoietic systems, caused by the hYAK3 imbalance including, but not limited to, neutropenia; cytopenia; anemias, including anemias due to renal insufficiency or to chronic disease, such as autoimmunity or cancer, and drug-induced anemias; polycythemia; and myelosuppression.

Another PSTK of importance in medicine is MK2 protein. Cytokines can induce many of the key features of inflammatory disease and inhibition of their production or mechanism of action would be an appropriate therapeutic approach. Inhibition of p38 MAP kinase has been demonstrated to decrease pro-inflammatory cytokine production including IL-1, TNF-α, IL-6, IL-8 and GMCSF. Inhibiting downstream of p38 may allow for greater selectivity towards these kinases implicated in up-regulation of pro-inflammatory cytokines and may lead to compounds with improved safety profiles. MAPKAP K2 (MK2) lies downstream and is directly activated by p38 MAP kinase. It has been established that MK2 and p38 exist as a complex in the nucleus and that phosphorylation of MK2 by p38 results in the export of this complex from the nucleus to the cytoplasm (Ben-Levy et al., Curr Biol 1998; 8:1049-57). Thus MK2 not only acts as a substrate but also as a determinant of the cellular localization of p38, which is consistent with a role for MK2 in both transcriptional and translational events Data from the MK2 knock-out mouse has demonstrated an important role for this kinase in pro-inflammatory cytokine production. MK2−/− knock-out mice exhibited a 90% reduction in LPS-induced TNF-α production and were resistant to endotoxic shock. Spleen cells from the MK2−/− mice also demonstrated significant inhibition of the pro-inflammatory cytokines TNF-α, IL-1β, IFN-γ and IL-6 following LPS stimulation (Kotlyarov et al., Nature Cell Biology 1999; 1:94-97). Compounds which are active against MK2 are believed to be useful in the treatment or prevention of rheumatoid arthritis, COPD, asthma, psoriasis, acute neuronal injury, heart failure, stroke, osteoarthritis, and ischemia reperfusion injury.

Compounds of the present invention are found to have activities against hYAK3 and/or MK2 proteins.

SUMMARY OF THE INVENTION

In a first aspect, the instant invention relates a method of inhibiting hYAK3 and/or MK2 in a mammal; comprising, administering to the mammal a therapeutically effective amount of a compound of the formula I, or a salt, solvate, or a physiologically functional derivative thereof

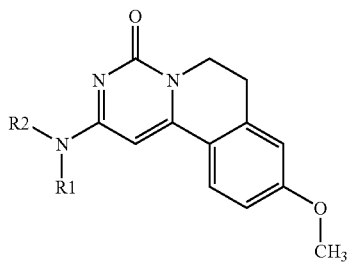

in which

R1 is hydrogen, —NH$_2$, or C$_{1-6}$alkyl;

R2 is hydrogen; or

R2 is a radical of the formula

in which W is a bond, —CH$_2$—, —CH$_2$CH$_2$—, —C(=O)—, —NCH$_3$—, or —NH—;

R is C$_{3-6}$cycloalkyl, C$_{1-6}$alkyl, hydroxy, —NH$_2$, (C$_{1-6}$alkyl)$_2$N—, C$_{1-6}$alkylO—, C$_{1-6}$alkylOCH$_2$—, phenyl optionally and independently substituted with one to three C$_{1-6}$alkyl, halogen, C$_{1-6}$alkylO—, C$_{1-6}$alkylOC(=O)—, acetyl, NH$_2$C(=O)—, FSO$_2$—, —CF$_3$, NH$_2$SO$_2$—, dimethylamino; HOCH$_2$—, CH$_3$NHC(=O)—, hydroxy, phenyl; or R is a radical of the formula

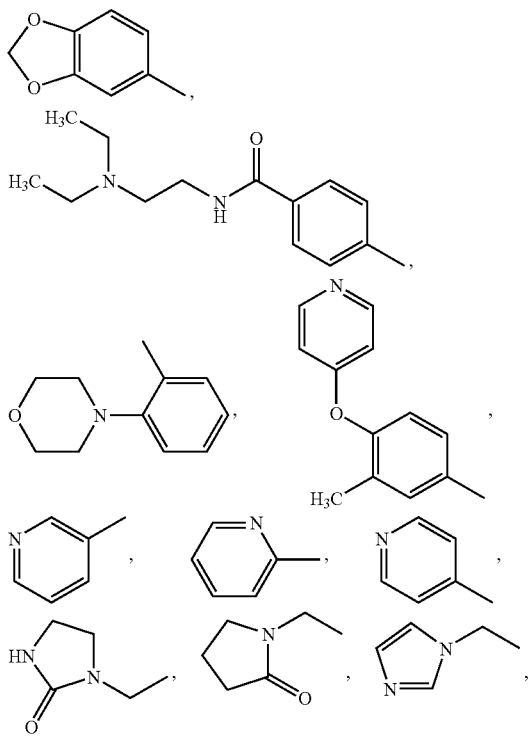

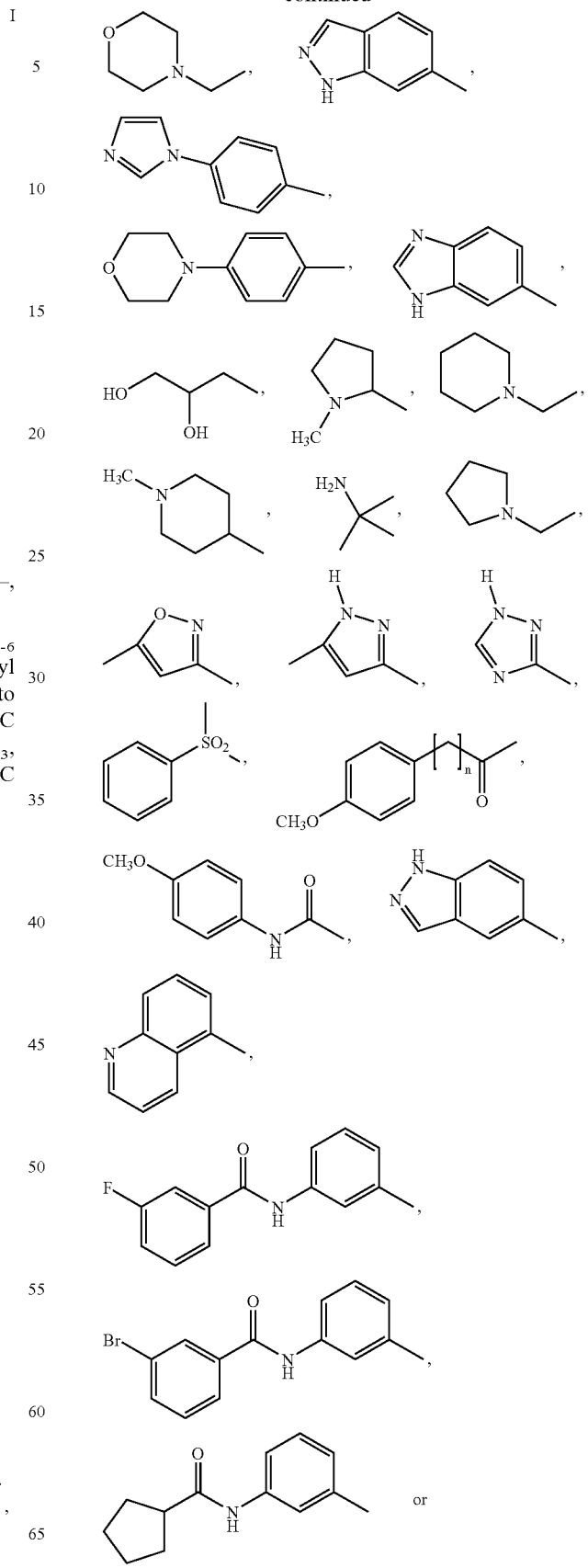

-continued

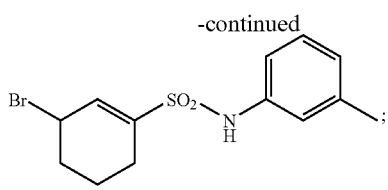

provided that W cannot be CH$_2$ when point of attachment of R to W is oxygen or nitrogen.

The preferred compounds of formula I is in which

R1 is hydrogen, or C$_{1-6}$alkyl;

R2 is hydrogen; or

R2 is a radical of the formula

in which W is a bond, —CH$_2$—, —CH$_2$CH$_2$—, —C(=O)—, —NCH$_3$—, or —NH—;

R is C$_{1-6}$alkyl, hydroxy, —NH$_2$, (C$_{1-6}$alkyl)$_2$N—, C$_{1-6}$alkylO—, C$_{1-6}$alkylOCH$_2$—, phenyl optionally and independently substituted with one to three C$_{1-6}$alkyl, halogen, C$_{1-6}$alkylO—, C$_{1-6}$alkylOC(=O)—, —CF$_3$, NH$_2$SO$_2$—, hydroxy, phenyl; or R is a radical of the formula

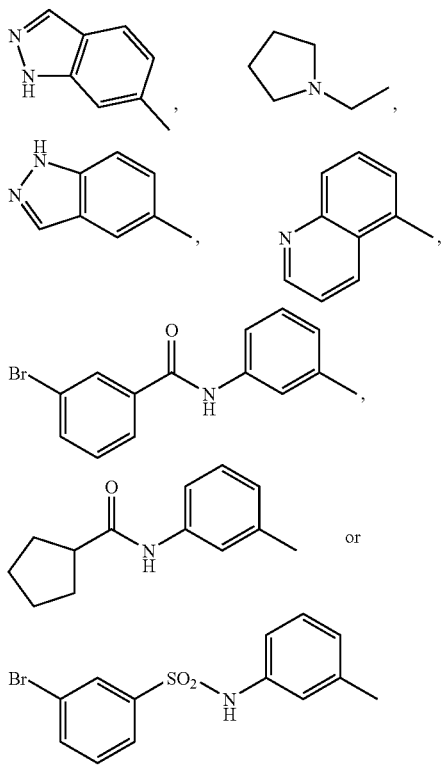

provided that W cannot be CH$_2$ when point of attachment of R to W is oxygen or nitrogen.

In a second aspect of the present invention, there is provided a pharmaceutical composition including a therapeutically effective amount of a compound of formula I, or a salt, solvate, or a physiologically functional derivative thereof and one or more of pharmaceutically acceptable carriers, diluents and excipients.

In a third aspect of the present invention, there is provided the use of a compound of formula I, or a salt, solvate, or a physiologically functional derivative thereof in the preparation of a medicament for use in the treatment or prevention of a disorder mediated by the imbalance or inappropriate activity of hYAK3 and/or MK2 proteins, including but not limited to, neutropenia; cytopenia; anemias, including anemias due to renal insufficiency or to a chronic disease, such as autoimmunity or cancer, and drug-induced anemias; polycythemia; myelosuppression; rheumatoid arthritis; COPD; asthma; psoriasis; acute neuronal injury; heart failure; stroke, osteoarthritris; and ischemia reperfusion injury.

In a fourth aspect, the present invention relates to a method of treating or preventing a disease, caused by the hYAK3 and/or MK2 imbalance or inappropriate activity including, but not limited to, neutropenia; cytopenia; anemias, including anemias due to renal insufficiency or to a chronic disease, such as autoimmunity or cancer, and drug-induced anemias; polycythemia; myelosuppression; rheumatoid arthritis; COPD; asthma; psoriasis; acute neuronal injury; heart failure; stroke, osteoarthritris; and ischemia reperfusion injury; comprising, administering to a mammal a therapeutically effective amount of a compound of formula I, or a salt, solvate, or a physiologically functional derivative thereof and one or more of pharmaceutically acceptable carriers, diluents and excipients.

In a fifth aspect, the present invention relates to a method of treating or preventing neutropenia; cytopenia; anemias, including anemias due to renal insufficiency or to a chronic disease, such as autoimmunity or cancer, and drug-induced anemias; polycythemia; myelosuppression; rheumatoid arthritis; COPD; asthma; psoriasis; acute neuronal injury; heart failure; stroke, osteoarthritris; and ischemia reperfusion injury; comprising, administering to a mammal a therapeutically effective amount of a compound of formula I, or a salt, solvate, or a physiologically functional derivative thereof and one or more of pharmaceutically acceptable carriers, diluents and excipients.

DETAILED DESCRIPTION

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the term "alkyl" refers to a straight or branched chain hydrocarbons. Thus, "C$_{1-6}$alkyl" refers to an alkyl group which contains at least 1 and at most 6 carbon atoms. Examples of "C$_{1-6}$alkyl" groups useful in the present invention include, but are not limited to, methyl, ethyl, propyl, isopropyl, isobutyl, n-butyl, n-pentyl, n-hexyl, and the like.

As used herein, the term "halogen" refers to fluorine (F), chlorine (Cl), bromine (Br), or iodine (I).

As used herein, the term "C$_{3-6}$cycloalkyl" refers to a non-aromatic cyclic hydrocarbon ring having from three to six carbon atoms. Exemplary "$C_{3-6}$cycloalkyl" groups include cyclopropyl, cyclobutyl, cyclopentyl, and cyclohexyl.

As used herein, the term "optionally" means that the subsequently described event(s) may or may not occur, and includes both event(s), which occur, and events that do not occur.

As used herein, the term "physiologically functional derivative" refers to any pharmaceutically acceptable derivative of a compound of the present invention, for example, an ester or an amide, which upon administration to a mammal is capable of providing (directly or indirectly) a compound of the present invention or an active metabolite thereof. Such derivatives are clear to those skilled in the art, without undue experimentation, and with reference to the teaching of Burger's Medicinal Chemistry And Drug Discovery, 5th Edition, Vol 1: Principles and Practice, which is incorporated herein by reference to the extent that it teaches physiologically functional derivatives.

As used herein, the term "solvate" refers to a complex of variable stoichiometry formed by a solute (in this invention, a compound of formula I or a salt or physiologically functional derivative thereof and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. Most preferably the solvent used is water.

As used herein, the term "substituted" refers to substitution with the named substituent or substituents, multiple degrees of substitution being allowed unless otherwise stated.

Certain of the compounds described herein may contain one or more chiral atoms, or may otherwise be capable of existing as two enantiomers. Accordingly, the compounds of this invention include mixtures of enantiomers as well as purified enantiomers or enantiomerically enriched mixtures. Also included within the scope of the invention are the individual isomers of the compounds represented by formula I above as well as any wholly or partially equilibrated mixtures thereof. The present invention also covers the individual isomers of the compounds represented by the formulas above as mixtures with isomers thereof in which one or more chiral centers are inverted. Also, it is understood that all tautomers and mixtures of tautomers are included within the scope of the compounds of formula I.

Typically, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts derived from a nitrogen on a substituent in the compound of formula I. Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate, triethiodide, trimethylammonium and valerate. Other salts, which are not pharmaceutically acceptable, may be useful in the preparation of compounds of this invention and these form a further aspect of the invention.

While it is possible that, for use in therapy, therapeutically effective amounts of a compound of formula I, as well as salts, solvates and physiological functional derivatives thereof, may be administered as the raw chemical, it is possible to present the active ingredient as a pharmaceutical composition. Accordingly, the invention further provides pharmaceutical compositions, which include therapeutically effective amounts of compounds of the formula I and salts, solvates and physiological functional derivatives thereof, and one or more pharmaceutically acceptable carriers, diluents, or excipients. The compounds of the formula I and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula I, or salts, solvates and physiological functional derivatives thereof, with one or more pharmaceutically acceptable carriers, diluents or excipients.

Pharmaceutical formulations may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the formula I, depending on the condition being treated, the route of administration and the age, weight and condition of the patient, or pharmaceutical formulations may be presented in unit dose forms containing a predetermined amount of active ingredient per unit dose. Preferred unit dosage formulations are those containing a daily dose or sub-dose, as herein above recited, or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including buccal or sublingual), rectal nasal topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the fling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of formula I, and salts, solvates and physiological functional derivatives thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of formula I, and salts, solvates and physiological functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered, dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the formulations may include other agents conventional in the art having regard to the type of formulation in question, for example those suitable for oral administration may include flavouring agents.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of a compound of formula I for the treatment of or prevention of diseases caused by hYAK3 and/or MK2 imbalance or inappropriate activity including, but not limited to, neutropenia; cytopenia; anemias, including anemias due to renal insufficiency or to a chronic disease, such as autoimmunity or cancer, and drug-induced anemias; polycythemia; myelosuppression; rheumatoid arthritis; COPD; asthma; psoriasis; acute neuronal injury; heart failure; stroke, osteoarthritris; and ischemia reperfusion injury; will generally be in the range of 0.1 to 100 mg/kg body weight of recipient (mammal) per day and more usually in the range of 1 to 10 mg/kg body weight per day. Thus, for a 70 kg adult mammal, the actual amount per day would usually be from 70 to 700 mg and this amount may be given in a single dose per day or more usually in a number (such as two, three, four, five or six) of sub-doses per day such that the total daily dose is the same. An effective amount of a salt or solvate, or physiologically functional derivative thereof, may be determined as a proportion of the effective amount of the compound of formula I per se. It is envisaged that similar dosages would be appropriate for treatment of the other conditions referred to above.

Method of Preparation

Compounds of general formula I may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) Protecting Groups in Organic Synthesis, John Wiley & Sons). These groups are removed at a convenient stage of the compound synthesis using methods that are readily apparent to those skilled in the art. The selection of processes as well as the reaction conditions and order of their execution shall be consistent with the preparation of compounds of formula I. Those skilled in the art will recognize if a stereocenter exists in compounds of formula I. Accordingly, the present invention includes both possible stereoisomers and includes not only racemic compounds but the individual enantiomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, Stereochemistry of Organic Compounds by E. L. Eliel, S. H. Wilen, and L. N. Mander (Wiley-Interscience, 1994).

More particularly, the compounds of the formula I can be made by the process of Scheme A or a variant thereof.

Examples which follow describe how some representative compounds of the present invention can be made according to the process described in Scheme A or a variant thereof.

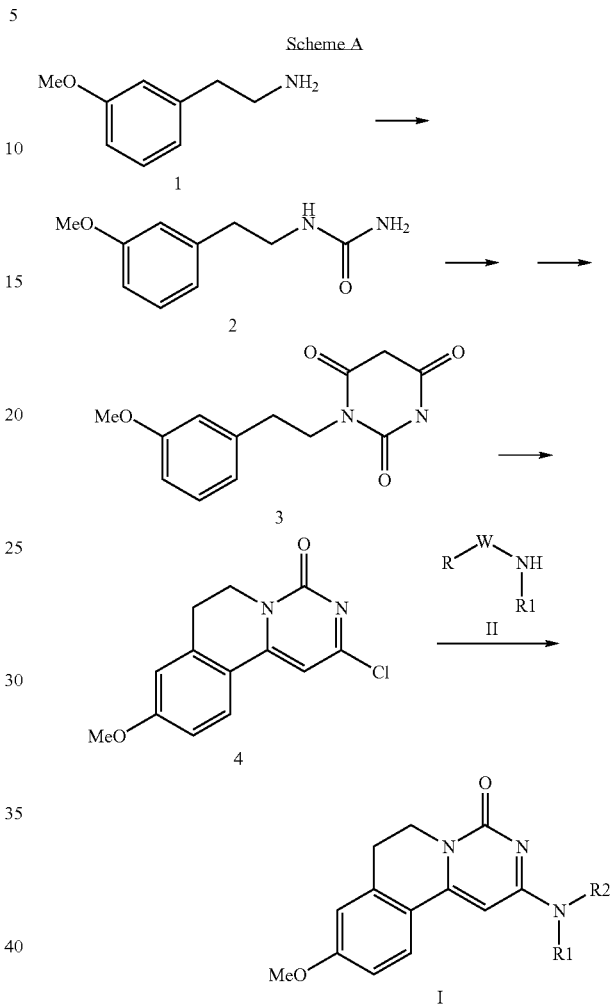

In Scheme A, the radicals R, W, R1, and R2 are as defined in formula I. As an example of a variant of process A for making a compound of formula I, a compound of formula II may need not be added to the compound of formula 4 in the last step, but rather a compound of formula HNR3R4 can be added. Here the radical —NR3R4 is a group which can be later converted to —NR1R2; few such variations are exemplified below.

SPECIFIC EMBODIMENTS—EXAMPLES

As used herein the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

g (grams); mg (milligrams);
L (liters); mL (milliliters);
μL (microliters); psi (pounds per square inch);
M (molar); mM (millimolar);
i. v. (intravenous); Hz (Hertz);
MHz (megahertz); mol (moles);
mmol (millimoles); rt (room temperature);
min (minutes); h (hours);
mp (melting point); TLC (thin layer chromatography);
Tr (retention time); RP (reverse phase);
MeOH (methanol); i-PrOH (isopropanol);
TEA (triethylamine); TFA (trifluoroacetic acid);
TFAA (trifluoroacetic anhydride); THF (tetrahydrofuran);
DMSO (dimethylsulfoxide); AcOEt (ethyl acetate);
DME (1,2-dimethoxyethane); DCM (dichloromethane);
DCE (dichloroethane); DMF (N,N-dimethylformamide);
DMPU (N,N'-dimethylpropyleneurea); CDI (1,1-carbonyldiimidazole);
IBCF (isobutyl chloroformate); HOAc (acetic acid);
HOSu (N-hydroxysuccinimide); HOBT (1-hydroxybenzotriazole);
mCPBA (meta-chloroperbenzoic acid; EDC (ethylcarbodiimide hydrochloride);
BOC (tert-butyloxycarbonyl); FMOC (9-fluorenylmethoxycarbonyl);
DCC (dicyclohexylcarbodiimide); CBZ (benzyloxycarbonyl);
Ac (acetyl); atm (atmosphere);
TMSE (2-(trimethylsilyl)ethyl); TMS (trimethylsilyl);
TIPS (triisopropylsilyl); TBS (t-butyldimethylsilyl);
DMAP (4-dimethylaminopyridine); BSA (bovine serum albumin)
ATP (adenosine triphosphate); HRP (horseradish peroxidase);
DMEM (Dulbecco's modified Eagle medium);
HPLC (high pressure liquid chromatography);
BOP (bis(2-oxo-3-oxazolidinyl)phosphinic chloride);
TBAF (tetra-n-butylammonium fluoride);
HBTU (O-Benzotriazole-1-yl-N,N,N',N'-tetramethyluronium hexafluorophosphate).
HEPES (4-(2-hydroxyethyl)-1-piperazine ethane sulfonic acid);
DPPA (diphenylphosphoryl azide);
fHNO3 (fumed HNO3); and
EDTA (ethylenediaminetetraacetic acid).

All references to ether are to diethyl ether; brine refers to a saturated aqueous solution of NaCl. Unless otherwise indicated, all temperatures are expressed in ° C. (degrees Centigrade). All reactions are conducted under an inert atmosphere at room temperature unless otherwise noted.

$^1$H NMR spectra were recorded on a Brucker AVANCE-400. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), quint (quintet), m (multiplet), br (broad). LC-MS were recorded on a micromass ZMD and Waters 2690. All mass spectra were taken under electrospray ionization (ESI) methods. Most of the reactions were monitored by thin-layer chromatography on 0.25 mm E. Merck silica gel plates (60F-254), visualized with UV light, 5% ethanolic phosphomolybdic acid or p-anisaldehyde solution. Flash column chromatography was performed on silica gel (230-400 mesh, Merck).

Example 1

2-(2,6-Dimethoxy-phenylamino)-9-methoxy-6,7-dihydro-pyrimido[6,1-a]isoquinolin-4-one (Ia)

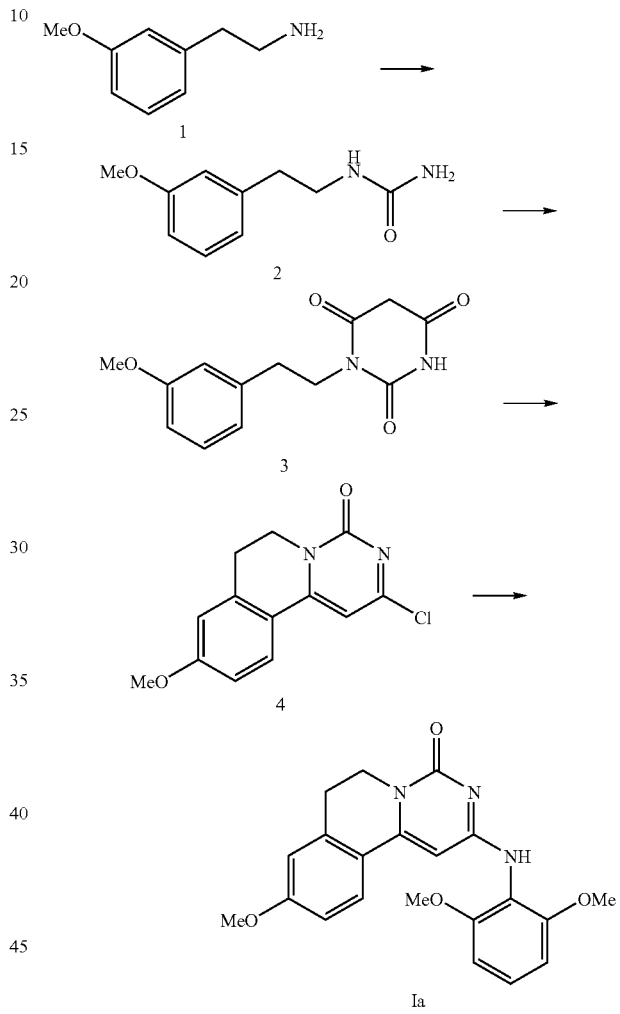

a. [2-(3-Methoxy-phenyl)-ethyl]-urea (2)

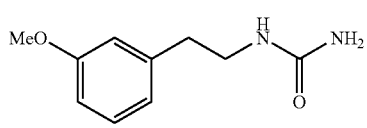

To a solution of 2-(3-methoxy-phenyl)-ethylamine (1) (50.0 g, 331 mmol) and concentrated HCl (27.6 mL) in water (350 mL), potassium cyanate (28.2 g, 348 mmol) was added and stirred at 50° C. for 2 hours, then at room temperature for 2 days. Formed precipitate was collected by filtration. The solid was washed with water and dried under reduced pressure to give the title compound (53.4 g, 83%). MS (ESI) (M+H)$^+$ 195.

b. 1-[2-(3-Methoxy-phenyl)-ethyl]-pyrimidine-2,4,6-trione (3)

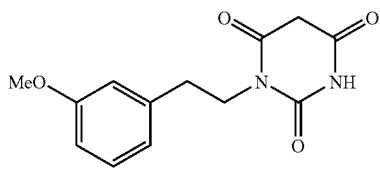

To a solution of NaOEt (144 mmol, fleshly prepared from 3.3 g of Na) in EtOH (80 mL), a solution of ethyl malonate (2) (22 mL, 144 mmol) in EtOH (250 mL) was added. The mixture was refluxed then added a solution of [2-(3-methoxy-phenyl)-ethyl]-urea (2) (23.3 g, 120 mmol) in EtOH (300 mL). The reaction mixture was refluxed overnight, then cooled to room temperature. The mixture was acidified carefully with 1M HCl aq. then poured into water (1 L). The precipitate which was formed was collected by filtration, washed with water then dried under reduced pressure to give the title compound (23.2 g, 74%). MS (ESI) (M+H)$^+$ 263.

c. 2-Chloro-9-methoxy-6,7-dihydro-pyrimido[6,7-a]isoquinolin-4-one (4)

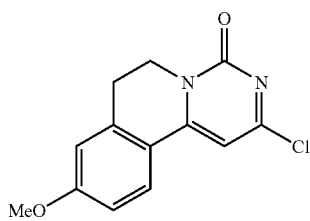

A suspension of 1-[2-(3-methoxy-phenyl)-ethyl]-pyrimidine-2,4,6-trione (3) (18.5 g, 70.3 mmol) in POCl$_3$ (175 mL) was stirred at 80° C. overnight. The solvent was removed by evaporation. To the residue, an ice-water was added, then basified with NaOH aq. The mixture was extracted with CH$_2$Cl$_2$ then the organic layer was dried over Na$_2$SO$_4$. After evaporation, the residue was recrystallized from MeOH to give the title compound (16.1 g, 87%). MS (ESI) (M+H)$^+$ 263.

d. 2-(2,6-Dimethoxy-phenylamino-9-methoxy-6,7-dihydro-pyrimido[6,1-a]isoquinolin-4-one (Ia)

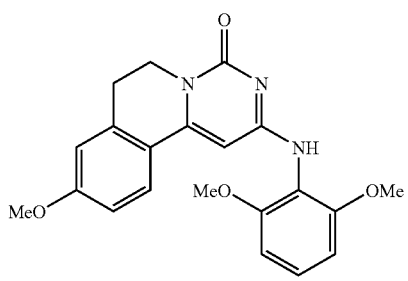

To a suspension of 2-chloro-9-methoxy-6,7-dihydro-pyrimido[6,1-a]isoquinolin-4-one (4) (105 mg, 0.4 mmol) in EtOH (10 mL), 2,6-dimethoxyaniline (153 mg, 1.0 mmol) was added and stirred at 75° C. overnight. After cooling, the mixture was purified on BondElut® SCX (Varian Incorporated) (then recrystallized from MeOH to give the title compound (31.4 mg, 21%). $^1$H-NMR (400 MHz, d$_6$-DMSO) δ 8.48 (s, 1H), 7.64 (br, 1H), 7.26 (t, 1H), 6.96 (s, 2H), 6.74 (d, 2H), 6.32 (br, 1H), 3.92 (t, 2H), 3.82 (s, 3H), 3.74 (s, 6H) and 2.93 (t, 2H); MS (ESI) (M+H)$^+$ 380.

Example 2

2-(1H-Indazol-5-ylamino)-9-methoxy-6,7-dihydro-pyrimido[6,1-a]isoquinolin-4-one (Ib)

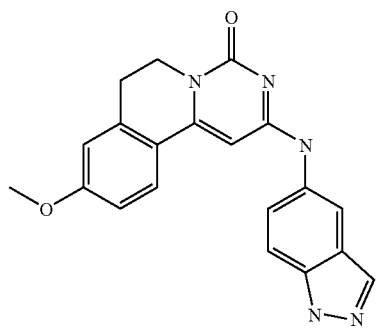

The title compound was prepared from 2-chloro-9-methoxy-6,7-dihydro-pyrimido[6,1-a]isoquinolin-4-one (4) and 1H-indazol-5-ylamine as in Example 1 d. $^1$H-NMR (400 MHz, d$_6$-DMSO) δ 13.00 (br, 1H), 9.60 (s, 1H), 8.36 (br, 1H), 8.06 (s, 1H), 7.69 (d, 1H), 7.51 (m, 2H), 7.10-6.95 (2H), 6.35 (s, 1H), 3.99 (t, 2H), 3.84 (s, 3H) and 2.97 (t, 2H); MS (ESI) (M+H)$^+$ 360.

Example 3

9-Methoxy-2-(2-methoxy-6-methyl-phenylamino)-6,7-dihydro-pyrimido[6,1-a]isoquinolin-4-one (Ic)

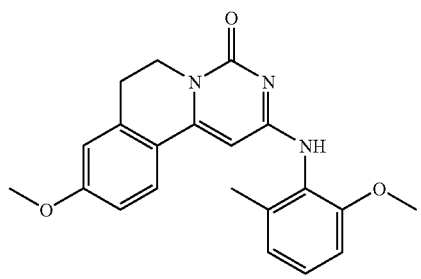

The title compound was prepared from 2-chloro-9-methoxy-6,7-dihydro-pyrimido[6,1-a]isoquinolin-4-one (4) and 2-methoxy-6-methyl-aniline as in Example 1 d. $^1$H-NMR (400 MHz, d$_6$-DMSO) δ 8.71 (br, 1H), 7.71 (br, 1H), 7.35-6.80 (5H), 6.39 (br, 1H), 3.92 (br, 2H), 3.83 (br, 3H), 3.74 (br, 3H), 2.94 (t, 2H) and 2.14 (br, 3H); MS (ESI) (M+H)$^+$ 364.

Example 4

2-(1H-Indazol-6-ylamino)-9-methoxy-6,7-dihydro-pyrimido[6,1-a]isoquinolin-4-one (Id)

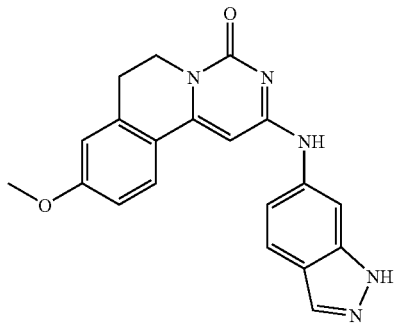

The title compound was prepared from 2-chloro-9-methoxy-6,7-dihydro-pyrimido[6,1-a]isoquinolin-4-one (4) and 1H-indazol-6-ylamine as in Example 1 d. $^1$H-NMR (400 MHz, d$_6$-DMSO) δ 12.95 (br, 1H), 9.76 (s, 1H), 8.60 (s, 1H), 7.96 (s, 1H), 7.72-7.60 (2H), 7.15-6.95 (3H), 6.42 (s, 1H), 4.01 (t, 2H), 3.85 (s, 3H) and 2.98 (t, 2H); MS (ESI) (M+H)$^+$ 360.

Example 5

2-(2-Bromo-phenylamino)-9-methoxy-6,7-dihydro-pyrimido[6,1-a]isoquinolin-4-one (Ie)

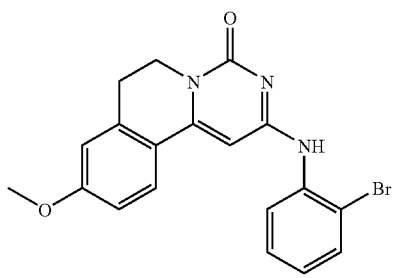

The title compound was prepared from 2-chloro-9-methoxy-6,7-dihydro-pyrimido[6,1-a]isoquinolin-4-one (4) and 2-bromo-aniline as in Example 1 d. $^1$H-NMR (400 MHz, d$_6$-DMSO) δ 9.06 (br, 1H), 7.76 (br, 1H), 7.69 (2H), 7.41 (t, 1H), 7.16 (t, 1H), 7.05-6.95 (2H), 6.47 (br, 1H), 3.96 (t, 2H), 3.84 (s, 3H) and 2.96 (t, 2H); MS (ESI) (M+H)$^+$ 398, 400.

Exmaple 6

3-(9-Methoxy-4-oxo-6,7-dihydro-4H-pyrimido[6,1-a]isoquinolin-2-ylamino)-benzenesulfonamide (If)

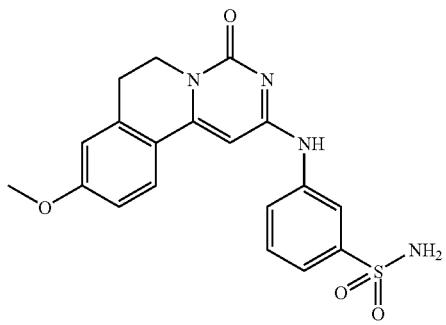

The title compound was prepared from 2-chloro-9-methoxy-6,7-dihydro-pyrimido[6,1-a]isoquinolin-4-one (4) and 3-amino-benzenesulfonamide as in Example 1 d. $^1$H-NMR (400 MHz, d$_6$-DMSO) δ 9.91 (s, 1H), 8.17 (d, 1H), 8.11 (s, 1H), 7.70 (d, 1H), 7.54 (t, 1H), 7.48 (d, 1H), 7.39 (br, 2H), 7.05-6.98 (2H), 6.37 (s, 1H), 4.00 (t, 2H), 3.85 (s, 3H) and 2.98 (t, 2H); MS (ESI) (M+H)$^+$ 399.

Example 7

2-(2-Chloro-phenylamino)-9-methoxy-6,7-dihydro-pyrimido[6,1-a]isoquinolin-4-one (Ig)

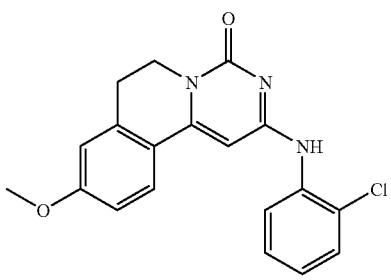

The title compound was prepared from 2-chloro-9-methoxy-6,7-dihydro-pyrimido[6,1-a]isoquinolin-4-one (4) and 2-chloro-aniline as in Example 1 d. $^1$H-NMR (400 MHz, d$_6$-DMSO) δ 9.10 (br, 1H), 7.91 (brd, 1H), 7.70 (brd, 1H), 7.53 (dd, 1H), 7.37 (t, 1H), 7.21 (t, 1H), 7.05-6.95 (2H), 6.55 (br, 1H), 3.97 (t, 2H), 3.84 (s, 3H) and 2.96 (t, 2H); MS (ESI) (M+H)$^+$ 354.

Example 8

2-(2,6-Dimethyl-phenylamino)-9-methoxy-6,7-dihydro-pyrimido[6,1-a]isoquinolin-4-one (Ih)

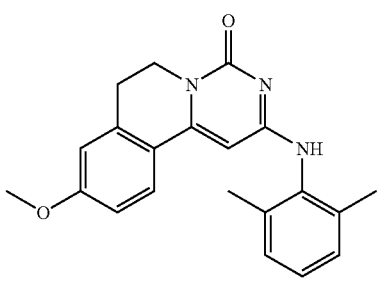

The title compound was prepared from 2-chloro-9-methoxy-6,7-dihydro-pyrimido[6,1-a]isoquinolin-4-one (4) and 2,6-dimethyl-aniline as in Example 1 d. $^1$H-NMR as two isomeric mixture (400 MHz, d$_6$-DMSO) δ 8.96 and 8.87 (br, 1H), 7.75 and 7.29 (d, 1H), 7.23-6.80 (5H), 6.37 and 5.33 (br, 1H), 3.96 and 3.92 (t, 2H), 3.84 and 3.78 (s, 3H), 2.95 (t, 2H) and 2.18 and 2.16 (s, 6H); MS (ESI) (M+H)$^+$ 348.

Example 9

2-(2-Bromo-6-fluoro-phenylamino)-9-methoxy-6,7-dihydro-pyrimido[6,1-a]isoquinolin-4-one (Ii)

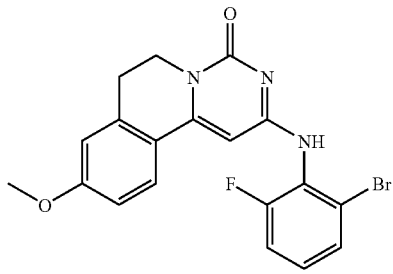

The title compound was prepared from 2-chloro-9-methoxy-6,7-dihydro-pyrimido[6,1-a]isoquinolin-4-one (4) and 2-bromo-6-fluoro-aniline as in Example 1 d. $^1$H-NMR (400 MHz, d$_6$-DMSO) δ 9.26 (br, 1H), 7.72 (br, 1H), 7.57 (brd, 1H), 7.34 (br, 2H), 7.05-6.95 (2H), 6.37 (br, 1H), 3.94 (t, 2H), 3.84 (s, 3H) and 2.96 (t, 2H); MS (ESI) (M+H)$^+$ 416, 418.

Example 10

2-(3-Methoxy-phenylamino)-9-methoxy-6,7-dihydro-pyrimido[6,1-a]isoquinolin-4-one (Ij)

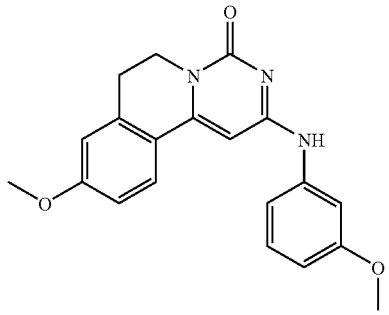

The title compound was prepared from 2-chloro-9-methoxy-6,7-dihydro-pyrimido[6,1-a]isoquinolin-4-one (4) and 3-methoxyaniline as in Example 1 d. $^1$H-NMR (400 MHz, d$_6$-DMSO) δ 9.59 (s, 1H), 7.68 (d, 1H), 7.52 (br, 1H), 7.30 (d, 1H), 7.23 (t, 1H), 7.05-6.95 (2H), 6.63 (dd, 1H), 6.35 (s, 1H), 3.98 (t, 2H), 3.84 (s, 3H), 3.75 (s, 3H) and 2.96 (t, 2H); MS (ESI) (M+H)$^+$ 350.

Example 11

2-(2-Hydroxy-6-methyl-phenylamino)-9-methoxy-6,7-dihydro-pyrimido[6,1-a]isoquinolin-4-one (Ik)

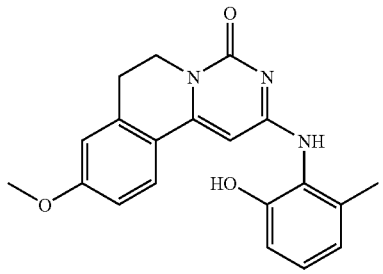

The title compound was prepared from 2-chloro-9-methoxy-6,7-dihydro-pyrimido[6,1-a]isoquinolin-4-one (4) and 2-hydroxy-6-methyl-aniline as in Example 1 d. $^1$H-NMR (400 MHz, d$_6$-DMSO, at 60° C.) δ 9.39 (br, 1H), 8.60 (br, 1H), 7.61 (br, 1H), 7.05-6.95 (3H), 6.75 (d, 1H), 6.73 (d, 1H), 6.34 (br, 1H), 3.95 (t, 2H), 3.83 (s, 3H), 2.95 (t, 2H), and 2.19 (s, 3H); MS (ESI) (M+H)$^+$ 350.

Example 12

9-Methoxy-2-(4-methoxy-biphenyl-3-ylamino)-6,7-dihydro-pyrimido[6,1-a]isoquinolin-4-one (Il)

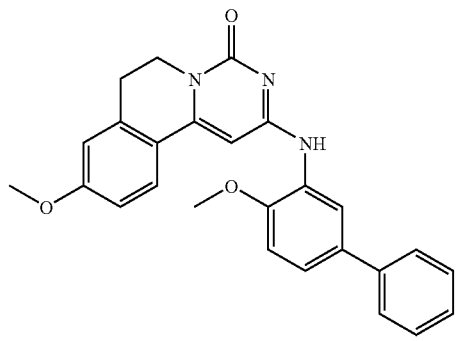

The title compound was prepared from 2-chloro-9-methoxy-6,7-dihydro-pyrimido[6,1-a]isoquinolin-4-one (4) and 3-amino-4-methoxy-biphenyl as in Example 1 d. $^1$H-NMR (400 MHz, d$_8$-DMSO) δ 8.85 (s, 1H), 8.55 (br, 1H), 7.70 (d, 1H), 7.60 (d, 2H), 7.46 (t, 2H), 7.38 (dd, 1H), 7.33 (t, 1H), 7.16 (d, 1H), 7.02 (dd, 1H), 6.98 (d, 1H), 6.72 (br, 1H), 3.97 (t, 2H), 3.91 (s, 3H), 3.84 (s, 3H) and 2.96 (t, 2H); MS (ESI) (M+H)$^+$ 426.

Example 13

3-(9-Methoxy-4-oxo-6,7-dihydro-4H-pyrimido[6,1-a]isoquinolin-2-ylamino)-benzoic acid ethyl ester (Im)

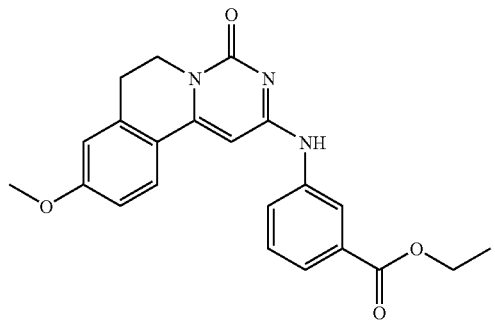

The title compound was prepared from 2-chloro-9-methoxy-6,7-dihydro-pyrimido[6,1-a]isoquinolin-4-one (4) and 3-amino-benzoic acid ethyl ester as in Example 1 d. ¹H-NMR (400 MHz, d₀-DMSO) δ 9.84 (s, 1H), 8.26 (s, 1H), 8.21 (d, 1H), 7.70 (d, 1H), 7.62 (d, 1H), 7.49 (t, 1H), 7.05-6.97 (2H), 6.36 (s, 1H), 4.33 (q, 2H), 3.99 (t, 2H), 3.85 (s, 3H), 2.97 (t, 2H) and 1.34 (t, 3H); MS (ESI) (M+H)⁺ 392.

Example 14

9-Methoxy-2-(2-methoxy-phenylamino)-6,7-dihydro-pyrimido[6,1-a]isoquinolin-4-one (In)

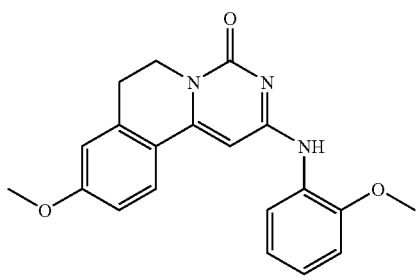

The title compound was prepared from 2-chloro-9-methoxy-6,7-dihydro-pyrimido[6,1-a]isoquinolin-4-one (4) and 2-methoxy-aniline as in Example 1 d. ¹H-NMR (400 MHz, d₆-DMSO) 88.74 (s, 1H), 8.24 (br, 1H), 7.69 (d, 1H), 7.12-6.92 (5H), 6.70 (br, 1H), 3.97 (t, 2H), 3.87 (s, 3H), 3.84 (s, 3H) and 2.96 (t, 2H); MS (ESI) (M+H)⁺ 350.

Example 15

9-Methoxy-2-(2-trifluoromethyl-phenylamino)-6,7-dihydro-pyrimido[6,1-a]isoquinolin-4-one (Io)

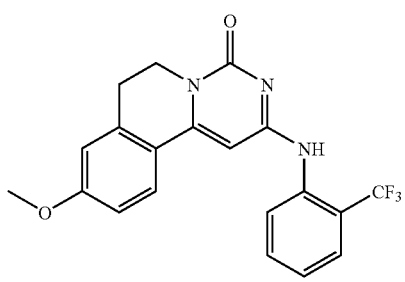

The title compound was prepared from 2-chloro-9-methoxy-6,7-dihydro-pyrimido[6,1-a]isoquinolin-4-one (4) and 2-trifluoromethyl-aniline as in Example 1 d. ¹H-NMR (400 MHz, d₆-DMSO) δ 9.10 (br, 1H), 7.90-7.35 (5H), 6.98 (2H), 6.42 (br, 1H), 3.94 (brt, 2H), 3.83 (s, 3H) and 2.95 (t, 2H); MS (ESI) (M+H)⁺ 388.

Example 16

2-(4-Chloro-2,6-dimethyl-phenylamino)-9-methoxy-6,7-dihydro-pyrimido[6,1-a]isoquinolin-4-one (Ip)

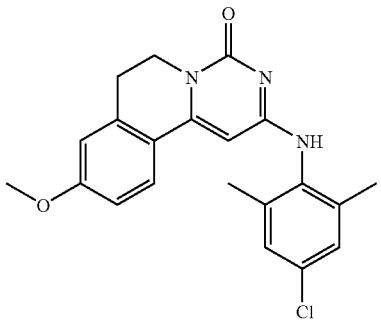

The title compound was prepared from 2-chloro-9-methoxy-6,7-dihydro-pyrimido[6,1-a]isoquinolin-4-one (4) and 4-Chloro-2,6-dimethyl-aniline as in Example 1 d. ¹H-NMR (400 MHz, d₆-DMSO) δ 8.73 (br, 1H), 7.72 (br, 1H), 7.19 (s, 2H), 7.03-6.95 (2H), 6.36 (br, 1H), 3.95 (t, 2H), 3.85 (s, 3H), 2.96 (t, 2H) and 2.18 (s, 6H); MS (ESI) (M+H)⁺ 382.

Example 17

9-Methoxy-2-(quinolin-5-ylamino)-6,7-dihydro-pyrimido[6,1-a]isoquinolin-4-one (Iq)

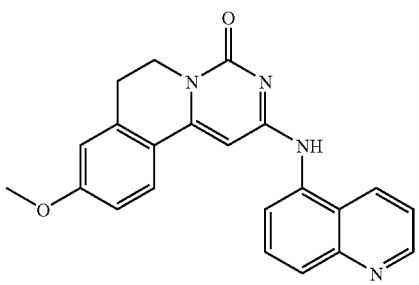

The title compound was prepared from 2-chloro-9-methoxy-6,7-dihydro-pyrimido[6,1-a]isoquinolin-4-one (4) and 5-amino-quinoline as in Example 1 d. ¹H-NMR (400 MHz, d₆-DMSO) δ 9.68 (br, 1H), 8.93 (dd, 1H), 8.47 (d, 1H), 7.89 (2H), 7.79 (t, 1H), 7.70 (d, 1H), 7.57 (dd, 1H), 7.03-6.97 (2H), 6.49 (br, 1H), 3.97 (t, 2H), 3.84 (s, 3H) and 2.97 (t, 2H); MS (ESI) (M+H)⁺ 371.

Example 18

2-(2-Chloro-6-methoxy-phenylamino)-9-methoxy-6,7-dihydro-pyrimido[6,1-a]isoquinolin-4-one (Ir)

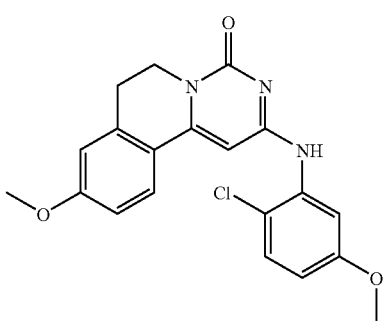

The title compound was prepared from 2-chloro-9-methoxy-6,7-dihydro-pyrimido[6,1-a]isoquinolin-4-one (4) and 2-chloro-5-methoxy-aniline as in Example 1 d. ¹H-NMR (400 MHz, d₆-DMSO) δ 8.99 (br, 1H), 7.76-7.60 (2H), 7.42 (d 1H), 7.05-6.95 (2H), 6.80 (dd, 1H), 6.60 (s, 1H), 3.97 (t, 2H), 3.84 (s, 3H), 3.76 (s, 3H) and 2.96 (t, 2H); MS (ESI) (M+H)⁺ 384.

Example 19

2-[N'-(2-Bromo-phenyl)-hydrazino]-9-methoxy-6,7-dihydro-pyrimido[6,1-a]isoquinolin-4-one (Is)

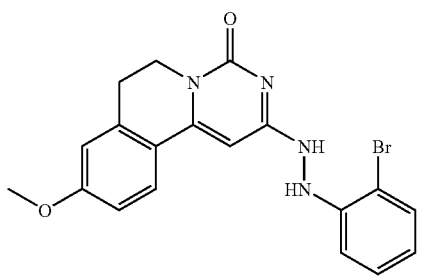

The title compound was prepared from 2-chloro-9-methoxy-6,7-dihydro-pyrimido[6,1-a]isoquinolin-4-one (4) and (2-bromo-phenyl)-hydrazine as in Example 1 d. ¹H-NMR (400 MHz, d₆-DMSO at 60° C.) δ 9.19 (br, 1H), 7.66 (brd, 1H), 7.46 (d, 1H), 7.44 (br, 1H), 7.20 (t, 1H), 6.98-6.75 (3H), 6.71 (t, 1H), 6.23 (s, 1H), 3.94 (t, 2H), 3.82 (s, 3H) and 2.93 (t, 2H); MS (ESI) (M+H)⁺ 413, 415.

Example 20

9-Methoxy-2-(N'-methyl-N'-phenyl-hydrazino)-6,7-dihydro-pyrimido[6,1-a]isoquinolin-4-one (It)

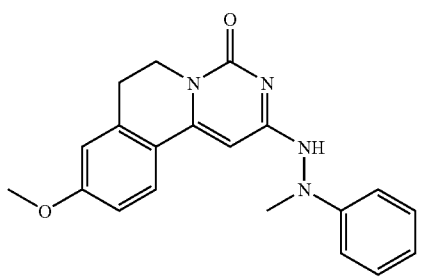

The title compound was prepared from 2-chloro-9-methoxy-6,7-dihydro-pyrimido[6,1-a]isoquinolin-4-one (4) and N-methyl-N-phenyl-hydrazine as in Example 1 d. ¹H-NMR (400 MHz, d₆-DMSO at 60° C.) δ 9.12 (br, 1H), 7.68 (d, 1H), 7.22 (t, 2H), 6.95-6.75 (5H), 6.24 (s, 1H), 3.96 (br, 2H), 3.82 (s, 3H), 3.16 (s, 3H) and 2.94 (t, 2H); MS (ESI) (M+H)⁺ 349.

Example 21

2-(2-Amino-ethylamino)-9-methoxy-6,7-dihydro-pyrimido[6,1-a]isoquinolin-4-one (Iu) HCl salt

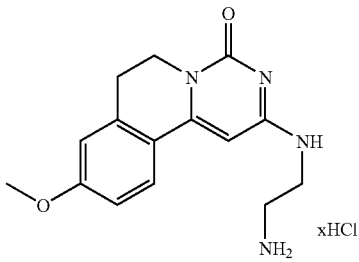

The title compound was prepared from 2-chloro-9-methoxy-6,7-dihydro-pyrimido[6,1-a]isoquinolin-4-one (4) and N-Boc-ethylenediamine as in Example 1 d, followed by treatment with HCl. ¹H-NMR as mixture of two isomers (400 MHz, d₆-DMSO) δ 9.25-8.40 (1H), 8.32 and 7.70 (d, 1H), 8.12 and 8.02 (br, 3H), 7.07-7.00 (m, 2H), 6.80 and 6.33 (s, 1H), 4.04 and 3.98 (t, 2H), 3.88 and 3.85 (s, 3H), 3.80 and 3.61 (q, 2H) and 3.08-2.94 (4H); MS (ESI) (M+H)⁺ 287. The spectrum acquired at 333K showed single isomers.

Example 22

9-Methoxy-2-(2-pyrrolidin-1-yl-ethylamino)-6,7-dihydro-pyrimido[6,1-a]isoquinolin-4-one (Iv) HCl salt

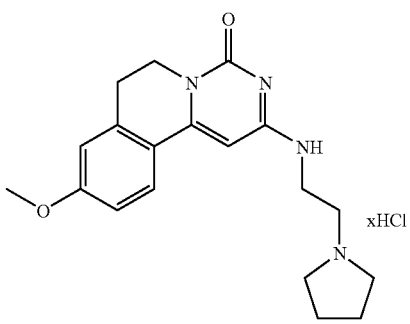

The title compound was prepared from 2-chloro-9-methoxy-6,7-dihydro-pyrimido[6, 1-a]isoquinolin-4-one (4) and 2-pyrrolidin-1-yl-ethylamine as in Example 1 d, followed by treatment with HCl. ¹H-NMR (400 MHz, dB-DMSO) δ 7.64 (d, 1H), 7.59 (br, 1H), 7.00-6.92 (2H), 6.18 (s, 1H), 3.92 (t, 2H), 3.82 (s, 3H), 3.46 (m, 2H), 2.91 (t, 2H), 2.90-2.50 (6H) and 1.76 (4H); MS (ESI) (M+H)⁺ 341.

Example 23

2-(2-Dimethylamino-ethylamino)-9-methoxy-6,7-dihydro-pyrimido[6,1-a]isoquinolin-4-one (Iw)

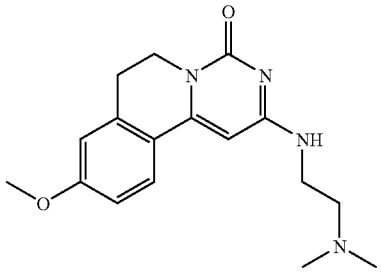

The title compound was prepared from 2-chloro-9-methoxy-6,7-dihydro-pyrimido[6,1-a]isoquinolin-4-one (4) and 2-dimethylamino-ethylamine as in Example 1 d. ¹H-NMR (400 MHz, d₆-DMSO) δ 7.81 (br, 1H), 7.78 (d, 1H), 7.01-6.95 (2H), 6.16 (s, 1H), 3.94 (t, 2H), 3.83 (s, 3H), 3.62 (br, 2H), 3.21 (br, 2H), 2.93 (t, 2H) and 2.83 (s, 6H); MS (ESI) (M+H)⁺ 315.

Example 24

2-(2-Hydroxy-ethylamino)-9-methoxy-6,7-dihydro-pyrimido[6,1-a]isoquinolin-4-one (Ix)

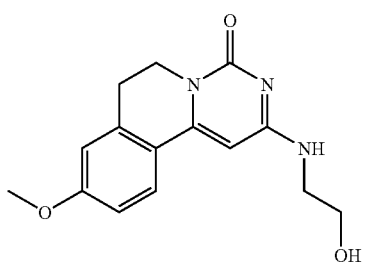

The title compound was prepared from 2-chloro-9-methoxy-6,7-dihydro-pyrimido[6,1-a]isoquinolin-4-one (4) and 2-hydroxy-ethylamine as in Example 1 d. ¹H-NMR (400 MHz, d₆-DMSO) δ 7.62 (d 1H), 7.54 (t, 1H), 7.00-6.93 (2H), 6.17 (s, 1H), 4.85 (t, 1H), 3.91 (t, 2H), 3.82 (s, 3H) 3.50 (q, 2H), 2.91 (t, 2H) and 2H were overlapped with H₂O; MS (ESI) (M+H)⁺ 288.

Example 25

9-Methoxy-2-[(2-methoxy-ethyl)-methyl-amino]-6,7-dihydro-pyrimido[6,1-a]isoquinolin-4-one (Iy) HCl salt

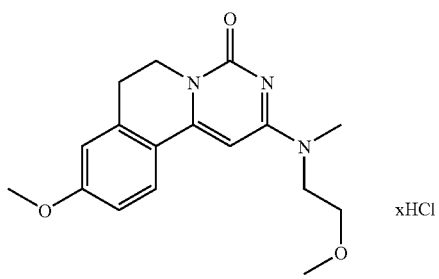

The title compound was prepared from 2-chloro-9-methoxy-6,7-dihydro-pyrimido[6,1-a]isoquinolin-4-one (4) and (2-methoxy-ethyl)-methyl-amine as in Example 1 d, followed by treatment with HCl. ¹H-NMR (400 MHz, d₆-DMSO, at 60° C.) δ 8.07 (d, 1H), 7.03-6.95 (2H), 6.56 (s, 1H), 4.00 (t, 2H), 3.86 (s, 3H), 3.86 (2H overlapped), 3.58 (t, 2H), 3.29 (s, 3H), 3.25 (s, 3H) and 3.00 (t, 2H); MS (ESI) (M+H)⁺ 316.

Example 26

9-Methoxy-2-(4-methoxy-benzylamino)-6,7-dihydro-pyrimido[6,1-a]isoquinolin-4-one (Iz)

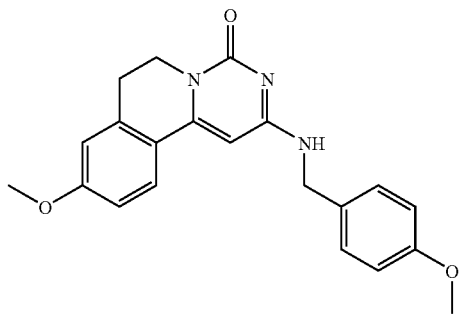

The title compound was prepared from 2-chloro-9-methoxy-6,7-dihydro-pyrimido[6,1-a]isoquinolin-4-one (4) and 4-methoxy-benzylamine as in Example 1 d. ¹H-NMR (400 MHz, d₆-DMSO) δ 7.89 (t, 1H), 7.63 (d, 1H), 7.25 (d, 2H), 7.0-6.93 (2H), 6.90 (d, 2H), 6.16 (s, 1H), 4.45 (d, 2H), 3.92 (t, 2H), 3.82 (s, 3H), 3.73 (s, 3H) and 2.92 (t, 2H); MS (ESI) (M+H)⁺ 364.

Example 27

9-Methoxy-2-(3-methoxy-benzylamino)-6,7-dihydro-pyrimido[6,1-a]isoquinolin-4-one (Iaa)

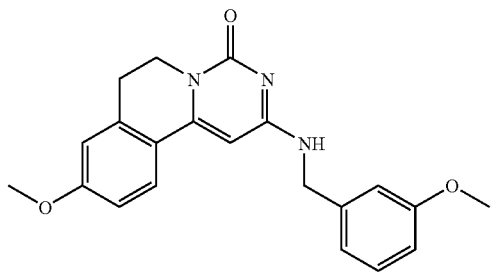

The title compound was prepared from 2-chloro-9-methoxy-6,7-dihydro-pyrimido[6,1-a]isoquinolin-4-one (4) and 3-methoxy-benzylamine as in Example 1 d. ¹H-NMR (400 MHz, d₆-DMSO) δ 7.95 (t, 1H), 7.65 (d, 1H), 7.25 (t, 1H), 7.00-6.85 (4H), 6.82 (dd, 1H), 6.19 (s, 1H), 4.50 (d, 2H), 3.92 (t, 2H), 3.82 (s, 3H), 3.74 (s, 3H) and 2.92 (t, 2H); MS (ESI) (M+H)⁺ 364.

Example 28

3-Bromo-N-[3-(9-methoxy-4-oxo-6,7-dihydro-4H-pyrimido[6,1-a]isoquinolin-2-ylamino)-phenyl]-benzamide (Iab)

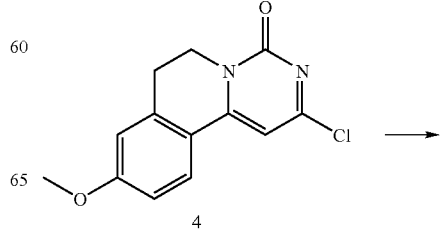

27

-continued

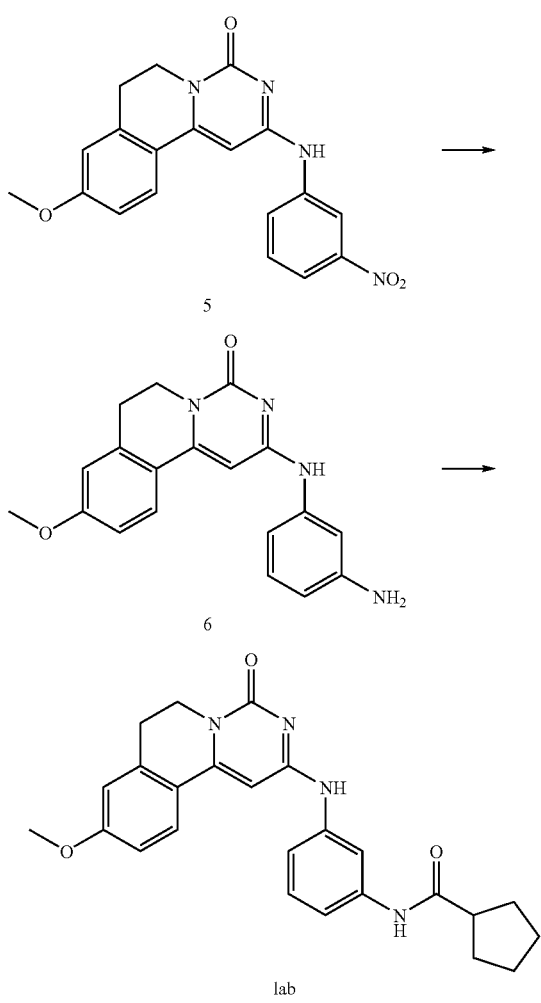

a. 2-(3-Nitro-phenylamino)-9-methoxy-6,7-dihydro-pyrimido[6,1-a]isoquinolin-4-one (5)

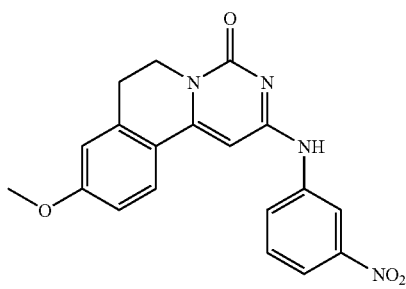

The title compound was prepared from 2-chloro-9-methoxy-6,7-dihydro-pyrimido[6,1-a]isoquinolin-4-one (4) and 3-nitro-aniline as in Example 1 d. $^1$H-NMR (400 MHz, d$_6$-DMSO) δ 10.10 (s, 1H), 8.87 (s, 1H), 8.13 (d, 1H), 7.88 (m, 1H), 7.73 (d, 1H), 7.63 (t, 1H), 7.02 (m, 2H), 6.38 (s, 1H), 4.01 (t, 2H), 3.85 (s, 3H) and 2.99 (t, 2H); MS (ESI) (M+H)$^+$ 365.

28 b. 2-(3-Amino-phenylamino)-9-methoxy-6,7-dihydro-pyrimido[6,1-a]isoquinolin-4-one (6)

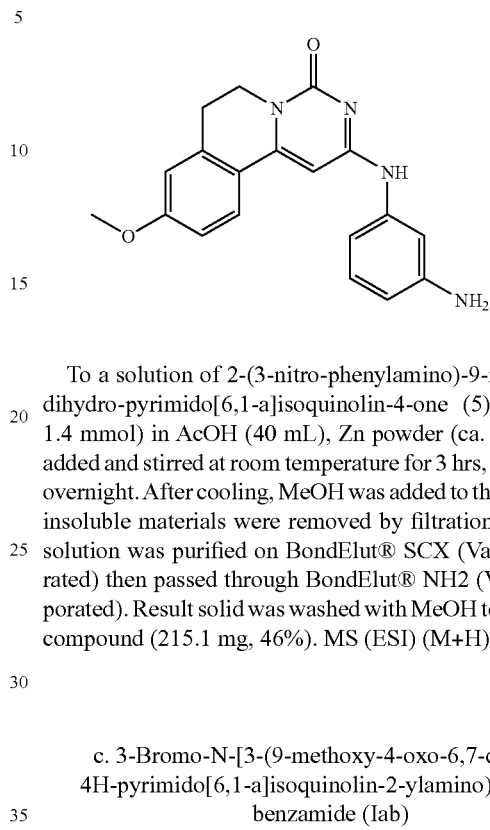

To a solution of 2-(3-nitro-phenylamino)-9-methoxy-6,7-dihydro-pyrimido[6,1-a]isoquinolin-4-one (5) (525.4 mg, 1.4 mmol) in AcOH (40 mL), Zn powder (ca. 300 mg) was added and stirred at room temperature for 3 hrs, then at 40° C. overnight. After cooling, MeOH was added to the mixture and insoluble materials were removed by filtration. The MeOH solution was purified on BondElut® SCX (Varian Incorporated) then passed through BondElut® NH2 (Variant Incorporated). Result solid was washed with MeOH to give the title compound (215.1 mg, 46%). MS (ESI) (M+H)$^+$ 335.

c. 3-Bromo-N-[3-(9-methoxy-4-oxo-6,7-dihydro-4H-pyrimido[6,1-a]isoquinolin-2-ylamino)-phenyl]-benzamide (Iab)

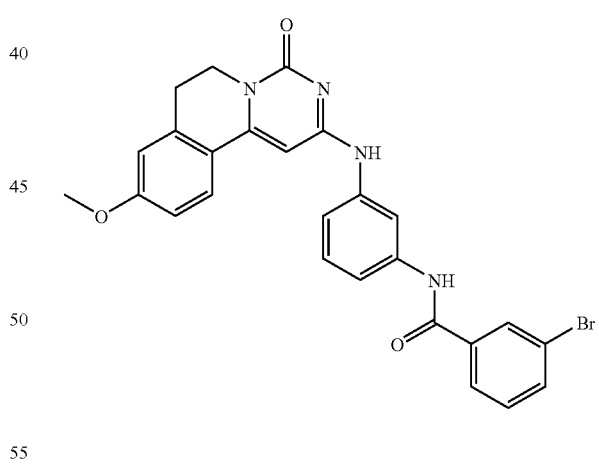

To a mixture of 2-(3-amino-phenylamino)-9-methoxy-6,7-dihydro-pyrimido[6,1-a]isoquinolin-4-one (§) (20.0 mg, 0.06 mmol) in THF (2 mL), triethylamine (13 μL, 0.09 mmol) and 3-bromobenzoylchloride (10 μL, 0.07 mmol) was added and stirred at 50° C. for 2 hrs. The mixture was quenched with concentrated HCl and purified on BondElut® SCX (Varian Incorporated). Formed solid was washed with CH$_2$Cl$_2$ to give the title compound (25.3 mg, 81%). $^1$H-NMR (400 MHz, d$^6$-DMSO) δ 10.43 (s, 1H), 9.68 (s, 1H), 8.15 (t, 1H), 8.08 (s, 1H), 7.97 (dt, 1H), 7.81 (ddd, 1H), 7.75 (brd, 1H), 7.70 (d, 1H), 7.51 (t, 1H), 7.36 (dt, 1H), 7.31 (t, 1H), 7.05-6.98 (2H), 6.42 (s, 1H), 3.99 (t, 2H), 3.84 (s, 3H) and 2.97 (t, 2H); MS (ESI) (M+H)+ 517, 519.

Example 29

Cyclopentanecarboxylic acid [3-(9-methoxy-4-oxo-6,7-dihydro-4H-pyrimido[6,1-a]isoquinolin-2-ylamino)-phenyl]-amide (Iac)

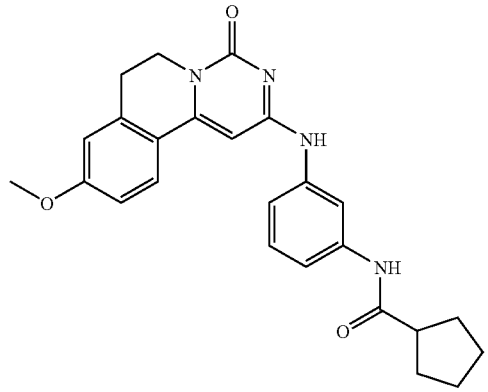

The title compound was prepared from 2-(3-amino-phenylamino)-9-methoxy-6,7-dihydro-pyrimido[6,1-a]isoquinolin-4-one (6) and cyclopentanecarbonyl chloride according the method described in Example 28 c. $^1$H-NMR (400 MHz, d$_6$-DMSO) δ 9.92 (s, 1H), 9.66 (br, 1H), 7.91 (s, 1H), 7.69 (d, 1H), 7.57 (br, 1H), 7.28-7.20 (2H), 7.05-6.97 (2H), 6.40 (s, 1H), 3.98 (t, 2H), 3.84 (s, 3H), 2.97 (t, 2H), 2.80 (m, 1H) and 1.92-1.50 (8H); MS (ESI) (M+H)+ 431.

Example 30

3-Bromo-N-[3-(9-methoxyy-4-oxo-6,7-dihydro-4H-pyrimido[6,1-a]isoquinolin-2-ylamino)-phenyl]-benzenesulfonamide (Iad)

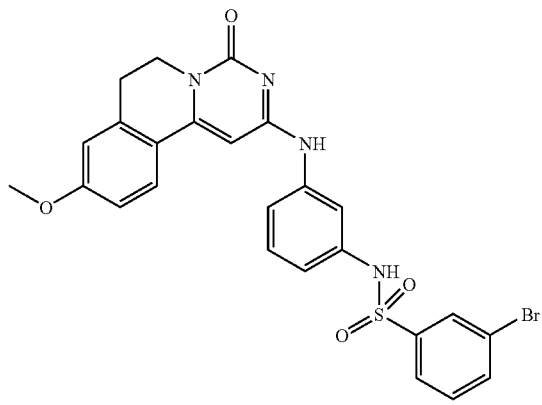

The title compound was prepared from 2-(3-amino-phenylamino)-9-methoxy-6,7-dihydro-pyrimido[6,1-a]isoquinolin-4-one (6) and 3-bromo-benzenesulfonyl chloride according to the method described in Example 28 c. $^1$H-NMR (400 MHz, d$_6$-DMSO) δ 10.47 (br, 1H), 9.62 (s, 1H), 7.95 (t, 1H), 7.91 (dt, 1H), 7.83 (ddd, 1H), 7.68 (d, 1H), 7.62-7.54 (2H), 7.53 (t, 1H), 7.18 (t, 1H), 7.05-6.97 (2H), 6.71 (dd, 1H), 6.34 (s, 1H), 3.99 (t, 2H), 3.84 (s, 3H) and 2.97 (t, 2H); MS (ESI) (M+H)+ 553, 555.

Example 31

2-Methoxy-N-(9-methoxy-4-oxo-6,7-dihydro-4H-pyrimido[6,1-a]isoquinolin-2-yl)-acetamide (Iae)

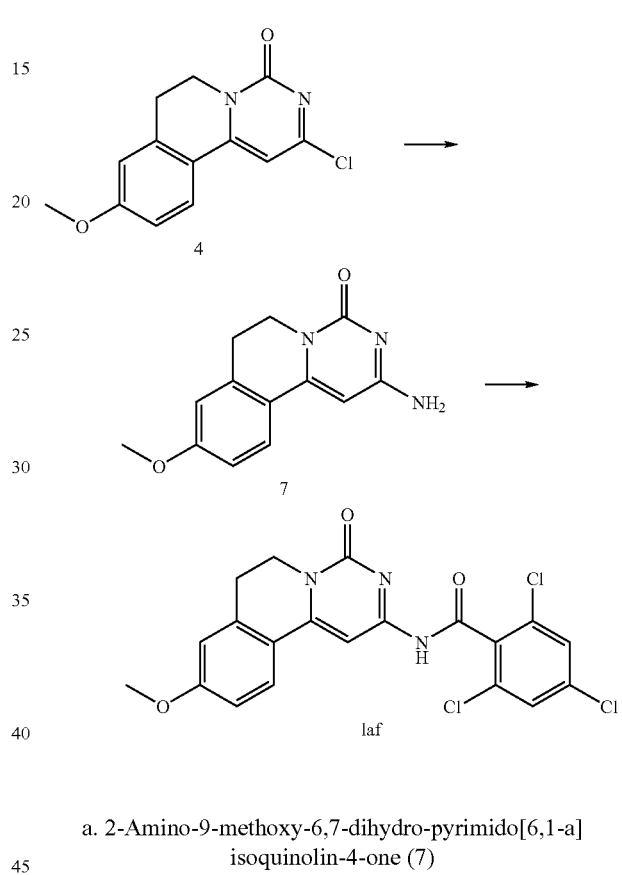

a. 2-Amino-9-methoxy-6,7-dihydro-pyrimido[6,1-a]isoquinolin-4-one (7)

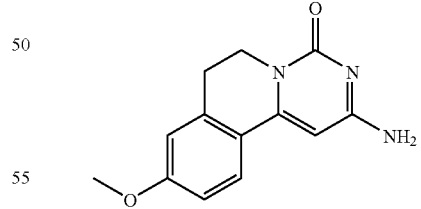

To a suspension of 2-chloro-9-methoxy-6,7-dihydro-pyrimido[6,1-a]isoquinolin-4-one (6) (919 mg, 3.5 mmol) in NH$_3$/EtOH (7 mL) was stirred in an autoclave at 120° C. overnight. After cooling, the precipitate was filtered and washed with MeOH to give the title compound (898.3 mg, quant.). $^1$H-NMR (400 MHz, d6-DMSO) δ 7.99 (b, 1H), 7.71 (d, 1H), 7.44 (b, 1H), 7.01 (dd, 1H), 7.00 (s, 1H), 6.22 (s, 1H), 3.95 (t, 2H), 3.85 (s, 3H) and 2.97 (t, 2H); MS (ESI) (M+H)+ 243.

b. 2,4,6-Trichloro-N-(9-methoxy-4-oxo-6,7-dihydro-4H-pyrimido[6,1-a]isoquinolin-2-yl)-benzamide (Iae)

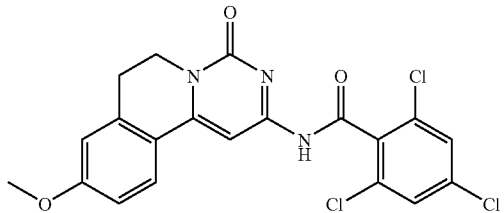

To a suspension of 2-amino-9-methoxy-6,7-dihydro-pyrimido[6,1-a]isoquinolin-4-one (7) (40 mg, 0.16 mmol) in $CHCl_3$ (3 mL), DMAP (30.1 mg, 0.24 mmol) and 2,4,6-trichlorobenzoyl chloride (37.5 uL, 0.24 mmol) was added and stirred at 25° C. overnight. After cooling, the mixture was purified on BondElut® SCX (Varian Incorporated) then column chromatography on silica gel ($CHCl_3$/MeOH=50/1 as eluant) to give the title compound (17.1 mg, 24%). $^1$H-NMR (400 MHz, $CDCl_3$) δ 7.90 (d, 1H), 7.42 (s, 2H), 6.95 (dd, 1H), 6.82 (d, 1H), 4.27 (t, 2H), 3.90 (s, 3.17) and 3.03 (t, 2H); MS (ESI) (M+H)$^+$ 449.

Example 32

2-Methoxy-N-(9-methoxy-4-oxo-6,7-dihydro-4H-pyrimido[6,1-a]isoquinolin-2-yl)-acetamide (Iaf)

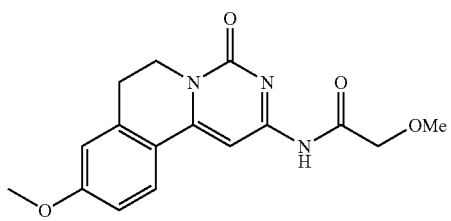

The title compound was obtained from 2-amino-9-methoxy-6,7-dihydro-pyrimido[6,1-a]isoquinolin-4-one (7) and methoxy-acetyl chloride according to the process described in Example 31 b. $^1$H-NMR (400 MHz, $d_6$-DMSO) δ 7.76 (d, 1H), 7.61 (s, 1H), 7.03 (dd, 1H), 7.02 (s, 1H), 4.10 (s, 2H), 4.06 (t, 3H), 3.85 (s, 1H) and 3.00 (t, 2H); MS (ESI) (M+H)$^+$ 315.

Biological Methods and Data

As demonstrated by the representative compounds in Tables 1 and 2, the compounds of the present invention have valuable pharmacological properties due to their ability to inhibit hYAK3 and/or MK2 kinase enzymes. The following are assay methods for measuring hYAK3 and MK2 inhibitory activity, respectively.

YAK3 Scintillation Proximity Assays Using Ser164 of Myelin Basic Protein as the Phosphoacceptor The source of Ser164 substrate peptide The biotinylated Ser164, S164A peptide (Biotinyl-LGGRDSRAGS*PMARR-OH), sequence derived from the C-terminus of bovine myelin basic protein (MBP) with Ser162 substituted as Ala162, was purchased from California Peptide Research Inc. (Napa, Calif.), and its purity was determined by HPLC. Phosphorylation occurs at position 164 (marked S* above). The calculated molecular mass of the peptide was 2166 dalton. Solid sample was dissolved at 10 mM in DMSO, aliquoted, and stored at −20° C. until use.

The source of enzyme:

hYAK3: Glutathione-S-Transferase (GST)-hYak3-His6 containing amino acid residues 124-526 of human YAK3 (aa 124-526 of SEQ ID NO 2. in U.S. Pat. No. 6,323,318) was purified from baculovirus expression system in Sf9 cells using Glutathione Sepharose 4B column chromatography followed by Ni-NTA-Agarose column chromatography. Purity greater than 65% typically was achieved. Samples, in 50 mM Tris, 150 mM NaCl, 10% glycerol, 0.1% Triton, 250 mM imidazole, 10 mM β-mercapto ethanol, pH 8.0. were stored at −80° C. until use.

Kinase assay of purified hYAK3: Assays were performed in 96 well (Costar, Catalog No. 3789) or 384 well plates (Costar, Catalog No. 3705). Reaction (in 20, 25, or 40 μl volume) mix contained in final concentrations 25 mM Hepes buffer, pH 7.4; 10 mM $MgCl_2$; 10 mM β-mercapto ethanol; 0.0025% Tween-20; 0.001 mM ATP, 0.1 μCi of [γ-$^{33}$P]ATP; purified hYAK3 (7-14 ng/assay; 4 nM final); and 4 μM Ser164 peptide. Compounds, titrated in DMSO, were evaluated at concentrations ranging from 50 μM to 0.5 nM. Final assay concentrations of DMSO did not exceed 5%, resulting in less than 15% loss of YAK3 activity relative to controls without DMSO. Reactions were incubated for 2 hours at room temperature and were stopped by a 75 ul addition of 0.19 μg Streptavidin Scintillation Proximity beads (Amersham Pharmacia Biotech, Catalog No. RPNQ 0007) in PBS, pH 7.4, 10 mM EDTA, 0.1% Triton X-100, 1 mM ATP. Under the assay conditions defined above, the $K_m$ (apparent) for ATP was determined to be 7.2+/−2.4 μM.

TABLE 1

| Example No. compounds | pIC$_{50}$ values |
|---|---|
| Ia | ++ |
| Iw | ++ |
| Iz | + |
| Ie | + |

Legend
| pIC$_{50}$ values | Symbol |
|---|---|
| 7.0-7.99 | ++ |
| 6.0-6.99 | + | pIC$_{50}$ = −log$_{10}$(IC$_{50}$)

MAPKAP2 Kinase (MK2) Enzyme Assay

Compounds are tested for MAPKAP2 kinase (MK2) inhibitory activity in an assay that measures the MK2 catalyzed transfer of the γ-phosphate from ATP to serine/threonine residues of a biotinylated peptide [NH2-K(biotin)-KL-NRTLSVA (SynPep Corporation, USA)]. Compounds under analysis are dissolved in DMSO to 1 mM and serially diluted 3-fold with DMSO in 96 or 384-well polypropylene or polystyrene plates for a total of 10-12 different concentrations. One uL of each concentration is transferred to the corresponding well of a 96 or 384-well, white, polystyrene assay plate. Reactions are performed in a final volume of 26 uL. An ATP solution (10 uL) is added to each well, and the reaction is initiated by the addition of a MK2/peptide mix (15 uL). The ATP solution is made in $H_2O$ and consists of 2.6 μM nonradioactive ATP (SigmaUltra) and 6.5 uCi/mL [γ-$^{33}$P]-ATP (Amersham Pharmacia Biotech). The MK2/peptide mix consists of 86.7 mM HEPES (SigmaUltra), pH 7.5, 8.67 mM MgCl$_2$ (SigmaUltra), 0.0043% Tween 20, 1.73 mM dithiothreitol (added fresh from frozen 1M stock), 1.73 µM peptide, and 1.73 nM purified recombinant MK2. Final concentrations of the assay components are 50 mM HEPES, pH 7.5, 5 mM MgCl$_2$, 0.0025% Tween 20, 1 mM dithiothreitol, 1 µM ATP, 2.5 µCi/mL [γ-$^{33}$P]-ATP, 1 µM peptide substrate, and 1 nM MK2. The reaction is allowed to proceed for 40 minutes and is then terminated by the addition of 'stop solution' (20 uL), followed by the addition of 'bead mix' (50 uL). The 'stop solution' consists of 50 mM HEPES, pH 8, 2.30 mM nonradioactive ATP, and 0.23M EDTA, and the 'bead solution' is PBS containing 3 mg/mL streptavidin-coated polyvinyltoluene SPA beads (Amersham Pharmacia Biotech). Under these conditions with no inhibitor, the reaction consumes approximately 15 percent of the peptide substrate and ATP. The plates are allowed to sit for approximately 8 hours and then are quantitated using a TopCount NXF™ (Packard). Alternatively, the plates are allowed to sit for at least approximately 1 hour, centrifuged at 900 rpm for 3 minutes, and then quantitated using a TopCount NXT™ (Packard). Controls are located within each assay plate, where the positive controls (signal$_{max}$) contain 1 uL of DMSO without compounds and the negative controls (signal$_{min}$) contain 1 uL of DMSO without compounds and an additional 4.5 uL of 0.5 M EDTA, pH 8 (Ivitrogen Corporation, GIBCO™). Percent inhibition of MK2 activity is calculated for each compound concentration using Equation [1]

$$\text{precent inhibition} = 100 * \left(1 - \frac{signal_{sample} - signal_{min}}{signal_{max} - signal_{min}}\right) \quad (1)$$

where signal$_{sample}$ is the signal observed in a particular sample well containing compound and signal$_{max}$ and signal$_{min}$ are defined above. The values used for signal$_{max}$ and signal$_{min}$ are averages of the corresponding control wells included within each plate. The data for each compound dose response is plotted as percent inhibition (y) versus compound concentration (x) and fitted by nonlinear regression to Equation [2]:

$$y = \left(\frac{V_{\max} * x}{K + x}\right) + Y2 \quad (2)$$

where Y2 is the baseline percent inhibition, V$_{max}$ is the net maximum percent inhibition (baseline subtracted), and K is the IC$_{50}$. Under the described assay conditions, the ATP concentration is well below the apparent ATP K$_m$, so IC$_{50}$ values are approximately equal to K$_i$ values. The results for each compound are recorded as pIC$_{50}$, calculated using Equation [3].

$$pIC_{50} = -\log_{10}(9IC_{50}) \quad (3)$$

TABLE 2

| Example No. compounds | pIC$_{50}$ values |
|---|---|
| Iv | ++ |
| Iy | ++ |
| If | + |

Legend

| pIC$_{50}$ values | Symbol |
|---|---|
| 7.0-8.0 | ++ |
| 6.00-6.99 | + |

UTILITY OF THE PRESENT INVENTION

The above biological data clearly shows that the compounds of formula I are useful for treating or preventing disease states in which hYAK3 and/or MK2 proteins are implicated including, but not limited to, neutropenia; cytopenia; anemias, including anemias due to renal insufficiency or to a chronic disease, such as autoimmunity or cancer, and drug-induced anemias; polycythemia; myelosuppression; rheumatoid arthritis; COPD; asthma; psoriasis; acute neuronal injury; heart failure; stroke, osteoarthritis; and ischemia reperfusion injury.

The compounds of formula I are especially useful in treating diseases of the hematopoietic system, particularly anemias. Such anemias include an anemia selected from the group comprising: aplastic anemia and myelodysplastic syndrome. Such anemias also include those wherein the anemia is a consequence of a primary disease selected from the group consisting of cancer, leukemia and lymphoma. Such anemias also include those wherein the anemia is a consequence of a primary disease selected from the group consisting of renal disease, failure or damage. Such anemias include those wherein the anemia is a consequence of chemotherapy or radiation therapy, in particular wherein the chemotherapy is chemotherapy for cancer or AZT treatment for HIV infection. Such anemias include those wherein the anemia is a consequence of a bone marrow transplant or a stem cell transplant. Such anemias also include anemia of newborn infants. Such anemias also include those which are a consequence of viral, fungal, microbial or parasitic infection.

The compounds of formula I are also useful for enhancing normal red blood cell numbers. Such enhancement is desirable for a variety of purposes, especially medical purposes such as preparation of a patient for transfusion and preparation of a patient for surgery.

What is claimed is:

1. A compound of the formula I, or a salt thereof

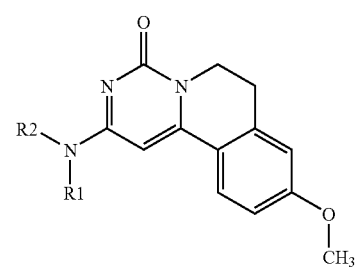

I in which

R1 is hydrogen, —NH$_2$, or C$_{1-6}$alkyl;

R2 is hydrogen; or

R2 is a radical of the formula

in which W is a bond, —CH$_2$—, —CH$_2$CH$_2$—, —C(=O)—, —NCH$_3$—, or —NH—;

R is phenyl optionally and independently substituted with one to three C$_{1-6}$alkyl, halogen, C$_{1-6}$alkylO—, C$_{1-6}$alkylOC(=O)—, acetyl, NH$_2$C(=O)—, FSO$_2$—, —CF$_3$, NH$_2$SO$_2$—, dimethylamino; HOCH$_2$—, CH$_3$NHC(=O)—, hydroxy, or phenyl; or R is a radical of the formula

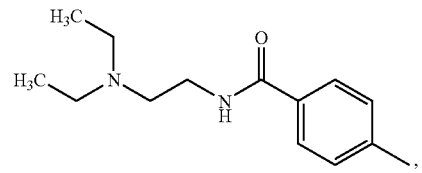

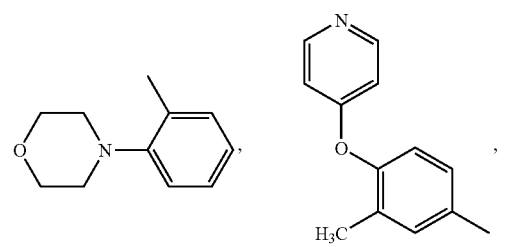

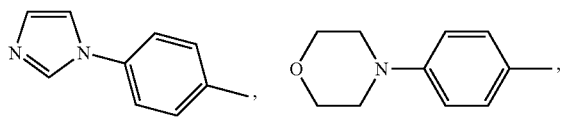

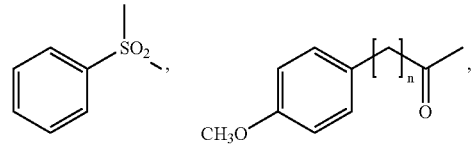

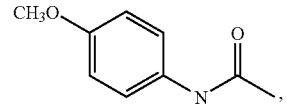

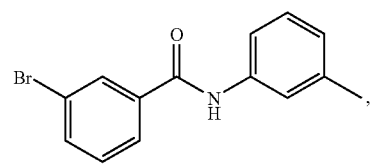

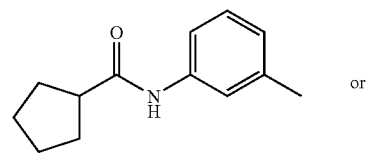

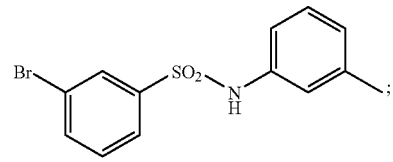

provided that W cannot be CH$_2$ when point of attachment of R to W is oxygen or nitrogen.

2. The compounds of formula I of claim 1 in which
R1 is hydrogen, or C$_{1-6}$alkyl;
R2 is hydrogen; or
R2 is a radical of the formula

in which W is a bond, —CH$_2$—, —CH$_2$CH$_2$—, —C(=O)—, —NCH$_3$—, or —NH—;
R is phenyl optionally and independently substituted with one to three C$_{1-6}$alkyl, halogen, C$_{1-6}$alkylO—, C$_{1-6}$alkylOC(=O)—, —CF$_3$, NH$_2$SO$_2$—, hydroxy, or phenyl; or
R is a radical of the formula

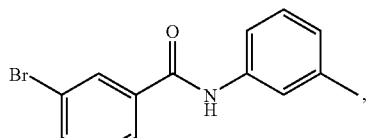

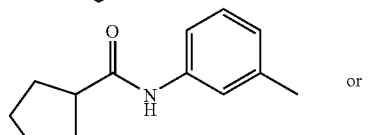  or

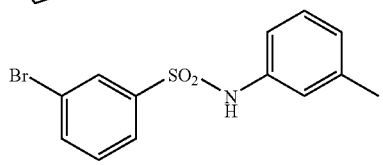

3. A compound of claim 1 that is 2-(2,6-dimethoxy-phenylamino)-9-methoxy-6,7-dihydro-pyrimido[6,1-a]isoquinolin-4-one.

4. A compound of claim 1 that is 9-methoxy-2-(2-methoxy-6-methyl-phenylamino)-6,7-dihydro-pyrimido[6,1-a]isoquinolin-4-one.

5. A compound of claim 1 that is 2-(2-bromo-phenylamino)-9-methoxy-6,7-dihydro-pyrimido[6,1-a]isoquinolin-4-one.

6. A compound of claim 1 that is 3-(9-methoxy-4-oxo-6,7-dihydro-4H-pyrimido[6,1-a]isoquinolin-2-ylamino)-benzenesulfonamide.

7. A compound of claim 1 that is 2-(2-chloro-phenylamino)-9-methoxy-6,7-dihydro-pyrimido[6,1-a]isoquinolin-4-one.

8. A compound of claim 1 that is 2-(2,6-dimethyl-phenylamino)-9-methoxy-6,7-dihydro-pyrimido[6,1-a]isoquinol;n-4-one.)

9. A compound of claim 1 that is 2-(2-bromo-6-fluoro-phenylamino)-9-methoxy-6,7-dihydro-pyrimido[6,1-a]isoquinolin-4-one.

10. A compound of claim 1 that is 2-(3-methoxy-phenylamino)-9-methoxy-6,7-dihydro-pyrimido[6,1-a]isoquinolin-4-one.

11. A compound of claim 1 that is 2-(2-hydroxy-6-methyl-phenylamino)-9-methoxy-6,7-dihydro-pyrimido[6,1-a]isoquinolin-4-one.

12. A compound of claim 1 that is 9-methoxy-2-(4-methoxy-biphenyl-3-ylamino)-6,7-dihydro-pyrimido[6,1-a]isoquinolin-4-one.

13. A compound of claim 1 that is 3-(9-methoxy-4-oxo-6,7-dihydro-4H-pyrimido[6,1-a]isoquinolin-2-ylamino)-benzoic acid ethyl ester.

14. A compound of claim 1 that is 9-methoxy-2-(2-methoxy-phenylamino)-6,7-dihydro-pyrimido[6,1-a]isoquinolin-4-one.

15. A compound of claim 1 that is 9-methoxy-2-(2-trifluoromethyl-phenylamino)-6,7-dihydro-pyrimido[6,1-a]isoquinolin-4-one.

16. A compound of claim 1 that is 2-(4-chloro-2,6-dimethyl-phenylamino)-9-methoxy-6,7-dihydro-pyrimido[6,1-a]isoquinolin-4-one.

17. A compound of claim 1 that is 2-(2-chloro-5-methoxyphenylamino)-9-methoxy-6,7-dihydro-pyrimido[6,1-a]isoquinolin-4-one.

18. A compound of claim 1 that is 2-[N'-(2-bromo-phenyl)-hydrazino]-9-methoxy-6,7-dihydro-pyrimido[6,1-a]isoquinolin-4-one.

19. A compound of claim 1 that is 9-methoxy-2-(N'-methyl-N'-phenyl-hydrazino)-6,7-dihydro-pyrimido[6,1-a]isoquinolin-4-one.

20. A compound of claim 1 that is 9-methoxy-2-(4-methoxy-benzylamino)-6,7-dihydro-pyrimido[6,1-a]isoquinolin-4-one.

21. A compound of claim 1 that is 9-methoxy-2-(3-methoxy-benzylamino)-6,7-dihydro-pyrimido[6,1-a]isoquinolin-4-one.

22. A compound of claim 1 that is 3-bromo-N-[3-(9-methoxy-4-oxo-6,7-dihydro-4H-pyrimido[6,1-a]isoquinolin-2-ylamino)-phenyl]-benzamide.

23. A compound of claim 1 that is cyclopentanecarboxylic acid [3-(9-methoxy-4-oxo-6,7-dihydro-4H-pyrimido[6,1-a]isoquinolin-2-ylamino)-phenyl]-amide.

24. A compound of claim 1 that is 3-bromo-N-[3-(9-methoxy-4-oxo-6,7-dihydro-4H-pyrimido[6,1-a]isoquinolin-2-ylamino)-phenyl]-benzenesulfonamide.

25. A compound of claim 1 that is 2,4,6-trichloro-N-(9-methoxy-4-oxo-6,7-dihydro-4H-pyrimido[6,1-a]isoquinolin-2-yl)-benzamide.

26. A compound of claim 1 that is 2-methoxy-N-(9-methoxy-4-oxo-6,7-dihydro-4H-pyrimido[6,1-a]isoquinolin-2-yl)-acetamide.

* * * * *